United States Patent [19]

Terada

[11] Patent Number: 5,140,757

[45] Date of Patent: Aug. 25, 1992

[54] ELASTIC BAND HEAT ACTIVATION SYSTEM

[76] Inventor: Stanley H. Terada, 2033 NE. 135th Pl., Seattle, Wash. 98125

[21] Appl. No.: 595,048

[22] Filed: Oct. 9, 1990

[51] Int. Cl.⁵ ............................................. F26B 19/00
[52] U.S. Cl. ........................................ 34/66; 34/216; 34/217
[58] Field of Search ............... 34/66, 65, 212, 213, 34/214, 222, 225, 216, 217

[56] References Cited

U.S. PATENT DOCUMENTS

| | | |
|---|---|---|
| 3,245,407 | 4/1966 | Mason . |
| 3,639,917 | 2/1972 | Althouse . |
| 3,727,324 | 4/1973 | Melgaard ........................... 34/66 X |
| 3,912,565 | 10/1975 | Koch et al. . |
| 4,300,967 | 11/1981 | Sigl . |
| 4,527,990 | 7/1985 | Sigl . |
| 4,563,185 | 1/1986 | Reiter . |
| 4,640,726 | 2/1987 | Sallee et al. . |
| 4,663,106 | 5/1987 | Pomplun et al. . |
| 4,665,306 | 5/1987 | Roland et al. . |
| 4,680,450 | 7/1987 | Thorson et al. . |
| 4,957,432 | 9/1990 | Rachal et al. ........................ 34/66 X |

FOREIGN PATENT DOCUMENTS

| | | |
|---|---|---|
| 1211602 | 9/1986 | Canada . |
| 0206349 | 12/1986 | European Pat. Off. . |
| 2016262A | 9/1979 | United Kingdom . |

Primary Examiner—Henry A. Bennet

[57] ABSTRACT

An elastic band activation apparatus for activating a heat-sensitive thermal film attached to an edge of a body of an article to form an elastic band along the edge of the article. The apparatus has at least one chamber with a heating zone having a shrinkage atmosphere at a first temperature sufficiently elevated to activate the heat-sensitive thermal film to shrink the film to form the elastic band. The chamber may also have a cooling zone with a quench atmosphere at a second temperature which is less than the first temperature to arrest the shrinkage of the heat-sensitive thermal film. An article transporter transports the article through the heating zone and then through the cooling zone. The apparatus may also include two lateral compression bars for spreading apart first and second adjacent edges of an article when transported through the chamber to expose the article interior region to activate first and second heat-sensitive thermal films, thereby forming first and second elastic bands. Alternate methods of forming elastic bands along an edge of an article are also provided.

11 Claims, 4 Drawing Sheets

ELASTIC BAND HEAT ACTIVATION SYSTEM

BACKGROUND OF THE INVENTION

The present invention relates generally to an elastic band heat activation system, including a method and apparatus for activating a heat-sensitive thermal film attached to an edge of a body of an article to form an elastic band along the edge of the article.

For example, the article may be an elasticized disposable headband or sweatband, a hospital surgical gown, a surgical hat, a pair of surgical booties, or a disposable incontinence garment, such as a disposable diaper with the elastic band formed thereon being a waistband. For the purposes of illustration, the finished product discussed herein will be a disposable diaper with an elastic waistband. It should be clear that the objects, techniques, features and advantages of the present invention may be applied to any such article to form an elastic band along the edge of the article.

Other activation systems have been used to activate a heat-shrinkable film located in a waistband portion of a disposable diaper to promote a high production rate without excessively heating the remaining portions of the diaper. These earlier systems included a continuous production apparatus having an enclosed heating zone in which hot air is blown toward the waistband portion of a plurality of disposable diapers, each having an elastic heat-shrinkable film attached thereto. The diapers are transported through the enclosed heating zone on an endless conveyor. To increase the energy efficiency of the system, the hot air is recycled. After heating the waistband, the diapers are allowed to cool to ambient temperature using the natural convection currents within a room where the diapers are located.

One known apparatus has an inverted U-shaped heating shroud through which the diapers are conveyed. The shroud has a plurality of jet openings for directing hot air jets toward the waistband portions of the diaper. The shroud may be automatically raised and lowered relative to the path of travel of the diapers to regulate the heat applied thereto. A greater volume of air is drawn off the diapers than the volume of hot air supplied to the waistband portions, so cooler ambient air is drawn over the remaining portions of the diapers and the components of the apparatus and extracted with the hot air.

In these known systems, the disposable diaper is folded along a transverse axis, so that the front waistband portion lies adjacent to the back waistband portion. The diapers are then transported in this state with the front and back waistband portions adjacent one another and directed toward the hot air source. Disadvantageously, the close proximity of the front and back waistband portions often prevents the hot air from entering the region of the diaper between the front and back waistband portions. This often results in non-uniform heating of the heat-shrinkable film which may cause improper shrinkage of the elastic, resulting in an inconsistent product.

After heating in these known systems, the gradual cooling to ambient temperature does not provide a controlled duration of heating. This uncontrolled heating duration may disadvantageously produce inconsistencies in the final finished products. Therefore, the earlier known systems often produce inconsistent products on a given assembly line, increasing the quality control problems for the article manufacturer, which in turn drives up the product cost.

Thus, a need exists for an improved elastic band heat activation system, including a method and apparatus, for activating a heat-sensitive thermal film attached to an edge of a body of an article to form an elastic band along the edge of the article, which is not susceptible to the above limitations and disadvantages.

SUMMARY OF THE INVENTION

It is an overall object of the present invention to provide an improved elastic band heat activation system for activating a heat-sensitive thermal film attached to an edge of a body of an article to form an elastic band along the edge of the article.

A further object of the present invention is to provide an improved elastic band heat activation apparatus for consistently producing a plurality of high quality articles having an elastic band along an edge of the article.

An additional object of the present invention is to provide an improved elastic band heat activation system which is energy efficient and cost effective to operate.

Another object of the present invention is to provide an improved method of activating a heat-sensitive thermal film attached to a first edge of a body of an article.

Still another object of the present invention is to provide an improved method of activating a heat-sensitive film which produces a plurality of articles having a consistently high quality elastic band along an edge of each article.

Yet another object of the present invention is to provide an improved method of activating a heat-sensitive film attached to an edge of a body of an article, the method being capable of implementation with current production methods of assembling of such articles.

According to one aspect of the present invention, an elastic band heat activation apparatus is provided for activating a heat-sensitive film attached to a first edge of a body of an article to form an elastic band along the first edge of the article. The apparatus includes at least one chamber having a heating zone with an atmosphere at a first temperature sufficiently elevated to activate the heat-sensitive thermal film to shrink the film to form an elastic band. The chamber also has a cooling zone with an atmosphere at a second temperature which is less than the first temperature. The apparatus includes an article transporter for transporting the article first through the heating zone to activate the heat-sensitive thermal film, and then through the cooling film to arrest the shrinkage of the heat-sensitive thermal film. In this manner, the elastic band is formed.

According to another aspect of the present invention, an elastic band heat activation apparatus for activating a thermal film as described above includes at least one chamber. The chamber has a heating zone with an atmosphere at a first temperature sufficiently elevated to activate the heat-sensitive thermal film to shrink the film to form an elastic band. The apparatus includes an article transporter for transporting the article through the heating zone to activate the film. The apparatus also has lateral compression means within the chamber for laterally compressing the body in a direction generally parallel to a first edge of the article along which the thermal film is attached. The body is laterally compressed while the article is transported by the article transporter through the heating zone, to aid in the formation of the elastic band.

According to a further aspect of the present invention, an elastic band heat activation apparatus for activating a thermal film as described above includes at least one chamber having a heating zone and a cooling zone as described above. The apparatus also includes an article transporter and lateral compression means, both as described above.

In an illustrated embodiment, the chamber comprises a common housing for at least partially enclosing both the heating and cooling zones. The chamber also has hot gas exhaust means for exhausting the heated gas as an exhaust gas after it has activated the thermal film. The apparatus also has hot gas recycling means coupled to the hot gas exhaust means for receiving the exhaust gas, reheating it and returning at least a portion of the reheated exhaust gas to the heating zone. Additionally, the heating zone may be divided into a preheating zone and a main heating zone. The preheating zone may receive the exhaust gas from the main heating zone, with or without being reheated. Monitoring means and control means responsive to the monitoring means are also provided for monitoring and controlling the apparatus.

According to yet another aspect of the present invention, a method is provided of activating a heat-sensitive thermal film attached to a first edge of a body of an article to form an elastic band along the first edge of the article. The method includes the steps of heating the first edge of the article to a first temperature sufficiently elevated to activate the heat-sensitive thermal film to shrink the film to form the elastic band. In a cooling step after the heating step, the first edge of the article is cooled to a second temperature which is less than the first temperature to arrest the shrinkage of the heat-sensitive film.

According to yet another aspect of the present invention, a method is provided of activating a heat-sensitive film as described above. The method includes the steps of heating the first edge of the article to a first temperature sufficiently elevated to activate the heat-sensitive thermal film to shrink the film to form the first elastic band. In a compressing step, the article is laterally compressed during the heating step to aid in formation of the first elastic band.

These and other objects, features and advantages of the present invention will become apparent to those skilled in the art from the following description and drawings.

DETAILED DESCRIPTION OF A PREFERRED EMBODIMENT

Figure 1:
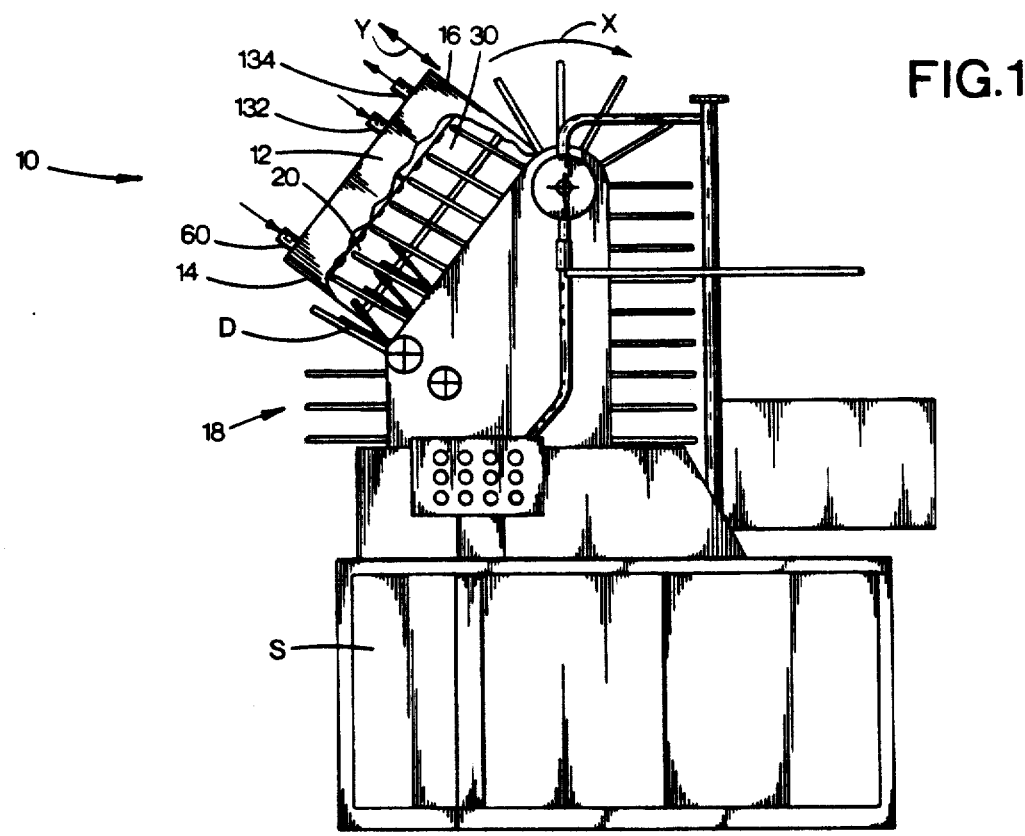
FIG. 1 is a side elevational view of one form of an elastic band heat activation apparatus of the present invention shown working in conjunction with a diaper stacking machine or diaper stacker which serves as an article transporter in this form of the present invention.
Figure 2:
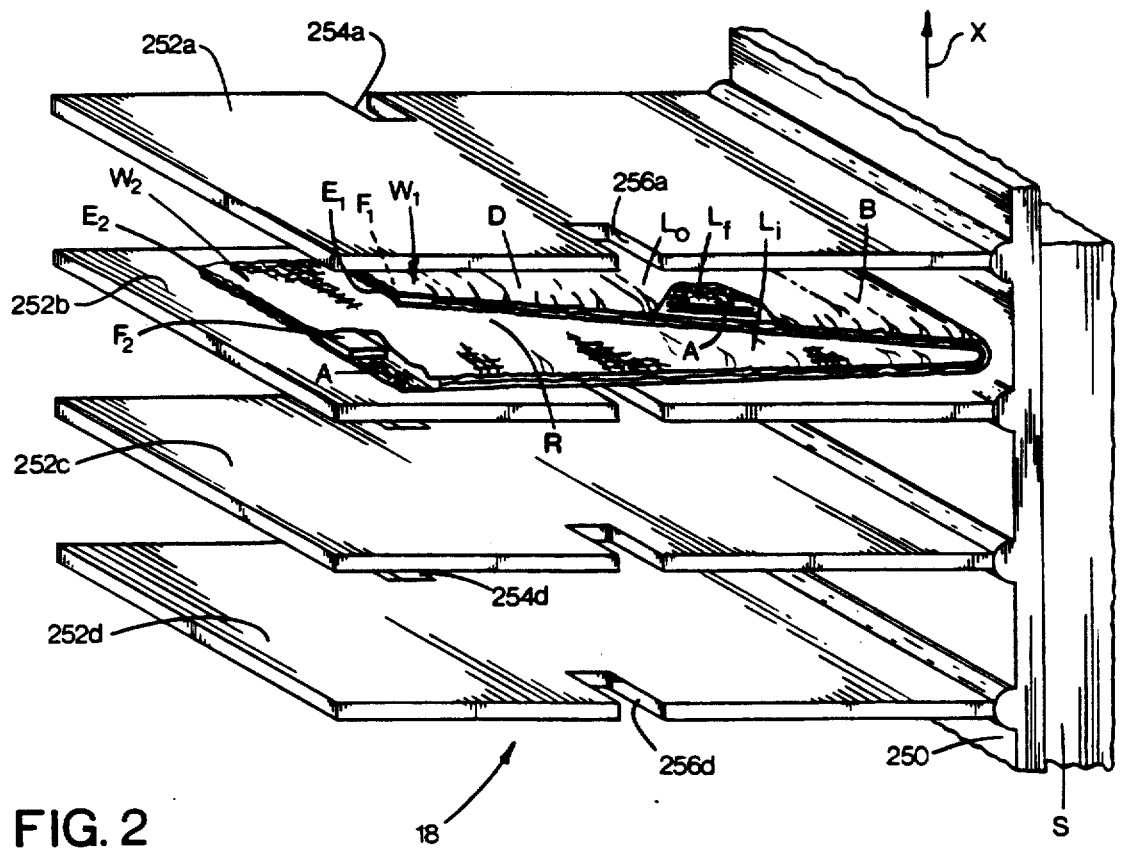
FIG. 2 is a partial, enlarged perspective view of the article transporter of FIG. 1.

FIG. 1 illustrates an embodiment of an elastic band heat activation apparatus 10 constructed in accordance with the present invention for forming an elastic band along an edge of an article. By way of illustration, the activation apparatus described is used to form an elasticized waistband W (FIG. 2) of a disposable diaper D having a body B. In FIG. 2, the diaper D is shown in a folded condition with edge $E_1$ adjacent edge $E_2$, defining an interior region R therebetween. The waistband portion W comprises front and back waistband portions $W_1$ and $W_2$ along respective edges $E_1$ and $E_2$.

Such disposable diapers typically have a moisture impervious outer sheet or layer $L_o$, and a moisture pervious non-woven body-contacting inner sheet or layer $L_i$. A moisture absorbent filler pad core or layer $L_f$ is sandwiched and encased between the inner and outer layers $L_i$ and $L_o$. The encasement of the diaper may be accomplished by bonding the layers together by plurality of fine hot melt adhesive lines (not shown).

The manufacture of disposable diapers is well known in the art. Once such diaper and method of manufacture is illustrated in U.S. Pat. No. 4,726,807 to Richard H. Young and Peter Lancaster, which is herein incorporated by reference to illustrate the typical materials used and methods of manufacturing such diapers.

For example, the moisture impervious outer layer $L_o$ may be of a thin thermal plastic material, such as a pigmented polyethylene film having a thickness in the range of 0.02–0.04 mm. The moisture pervious inner layer $L_i$ may typically be of a carded polyester fiber with a latex binder or of a spun-bonded polypropylene having continuous fibers and thermally bonded by patterned calendar rolls. The moisture absorbent layer $L_f$ may be of any suitable material with fibrous materials commonly being used. For example, wood fibers or other fibers, such as chemical wood pulp, or any other suitable liquid absorbing material, such as commercially available fluff pulp, or of a fluffed bleached kraft softwood pulp may be used with or without other fibers and liquid absorbing chemicals. The hot melt adhesive lines (not shown) may be of the flexible rapid setting variety, such as those formulated from ethylene-vinyl acetate resins used with tackifiers and other additives.

To assemble the waistband portions $W_1$ and $W_2$, fine lines of adhesive A (FIG. 2), which may be of the hot melt variety described above, are applied to the inner side of one or both of the inner and outer layers $L_i$ and $L_o$ along the waistband edges $E_1$ and $E_1$. Although not shown in FIG. 2, waistband $W_1$ is constructed in the same manner as illustrated for waistband $W_2$. Strips $F_1$ and $F_2$ of a heat-sensitive thermal film F are sandwiched between the inner and outer layers $L_i$ and $L_o$ along the respective waistband edges $E_1$ and $E_2$ using the fine lines of adhesive A. Upon exposure to heat, the film F contracts to form an elastic band along the edge of the article, here along the waistband portion W of diaper D.

One suitable heat-sensitive thermal film F is known as Fulflex Blend III, which may be obtained from the Fulflex Company, P.O. Box 4549, Middletown, R.I. 02840. Suitable dimensions for the film strip may be a nominal thickness of 1 mil (0.001 inches) 50 mm long and 12.7 mm wide. For elasticized diaper waistbands, the ability of the elastic waistband to return to the original contracted form after being stretched to a maximum elongation may be a 5–9% memory loss (with a nominal value of 7%). An ideal tension value, that is the amount of force needed to deflect the waistband to eighty percent of the difference between the minimum and maximum stretch, may be on the order of 260 to 300 grams (with a nominal value of 280 grams). The percent elasticity (or shrinkage), that is, the increase in width of the waistband from a relaxed position to the waistband ultimate width, may be on the order of 20–30%. These characteristics are of course variable.

The activation apparatus 10 includes a housing or shroud 12 having an entrance end 14 and an exit end 16. A diaper stacking machine or diaper stacker S serves as an article transporter 18 for transporting the diapers in a direction indicated by arrow X through shroud 12 from the entrance end 14 to the exit end 16. The shroud 12 may be permanently attached to the stacker S or the shroud may be raised and lowered from the stacker in a direction indicated by arrow Y using hydraulic, pneumatic, or other actuating means (not shown).

Figure 3:
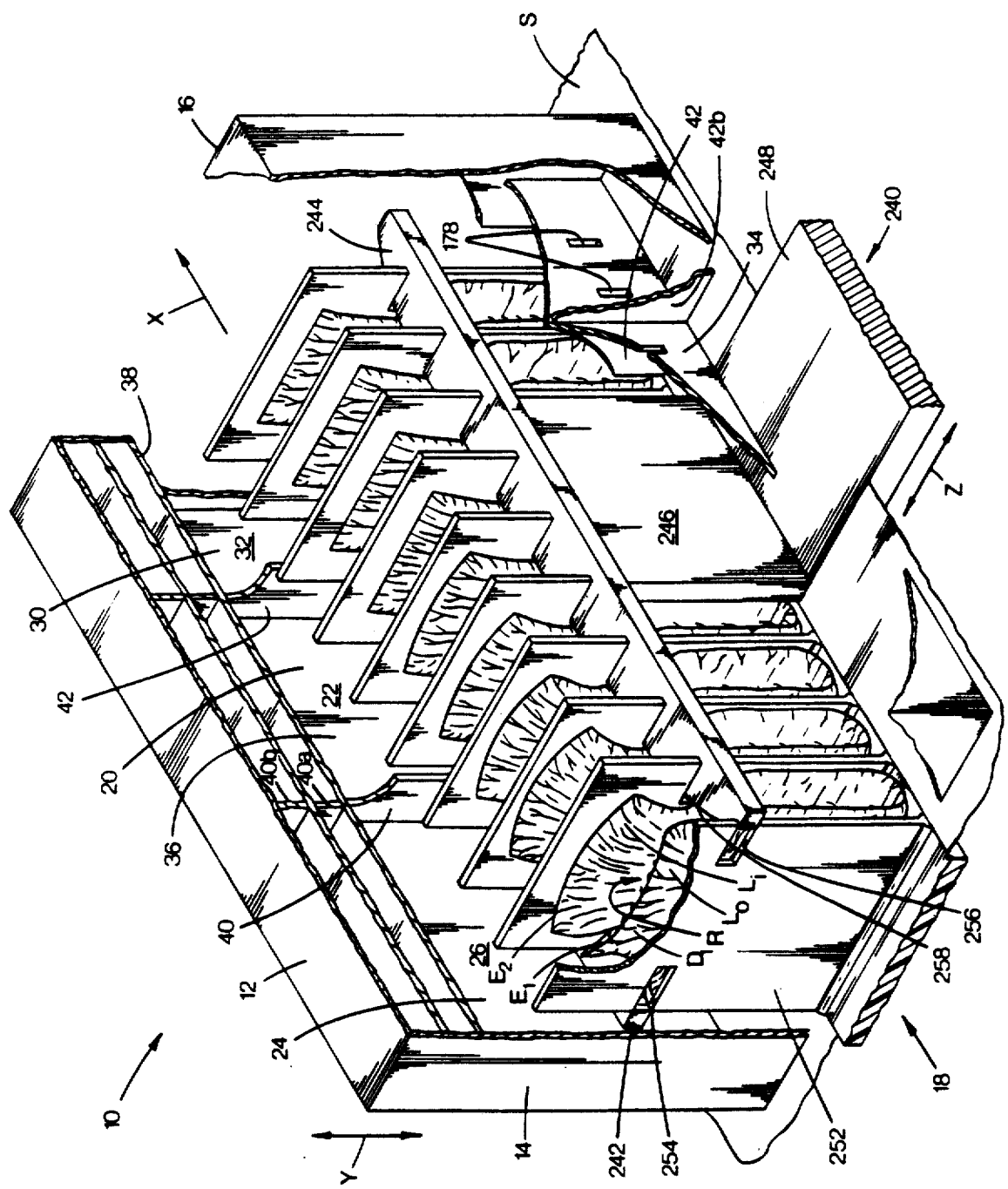
FIG. 3 is an enlarged partially cutaway perspective view of one form of a chamber of an elastic band heat activation apparatus of the present invention.

Referring to FIG. 3, the illustrated shroud 12 defines at least one chamber, such as a heating chamber 20 for at least partially enclosing a main heating stage or zone 22. To enhance the efficiency of the activation apparatus 10, the shroud 12 may also define a preheat chamber 24 for at least partially enclosing a preheating stage or zone 26. The preheating zone 26 is located adjacent the shroud entrance 14. The activation apparatus 10 may also include a cooling or quench chamber 30, such as that defined by shroud 12. The cooling chamber 30 is located adjacent the shroud exit end 16, and defines therein a quench or cooling stage or zone 32.

Figure 4:
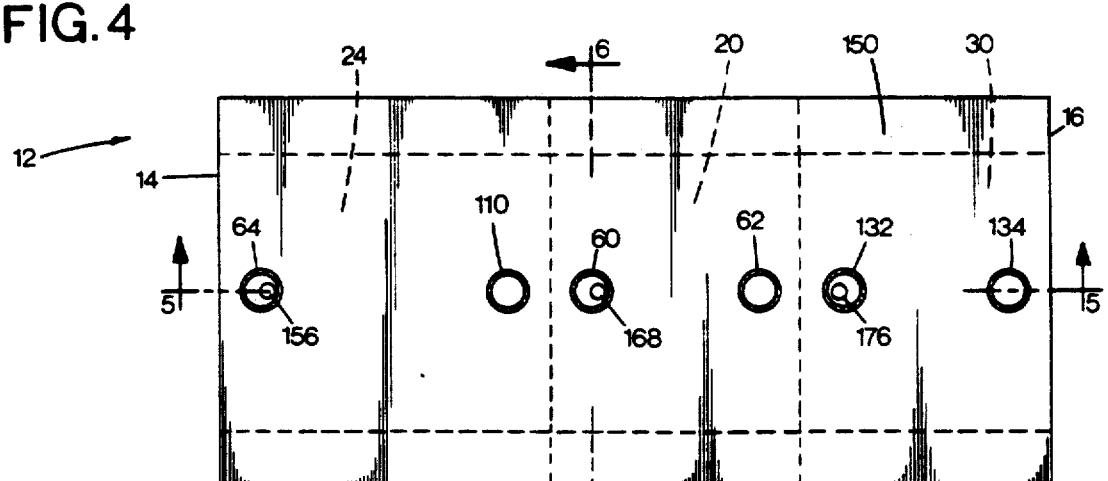
FIG. 4 is a top plan view of the chamber of FIG. 3.
Figure 5:
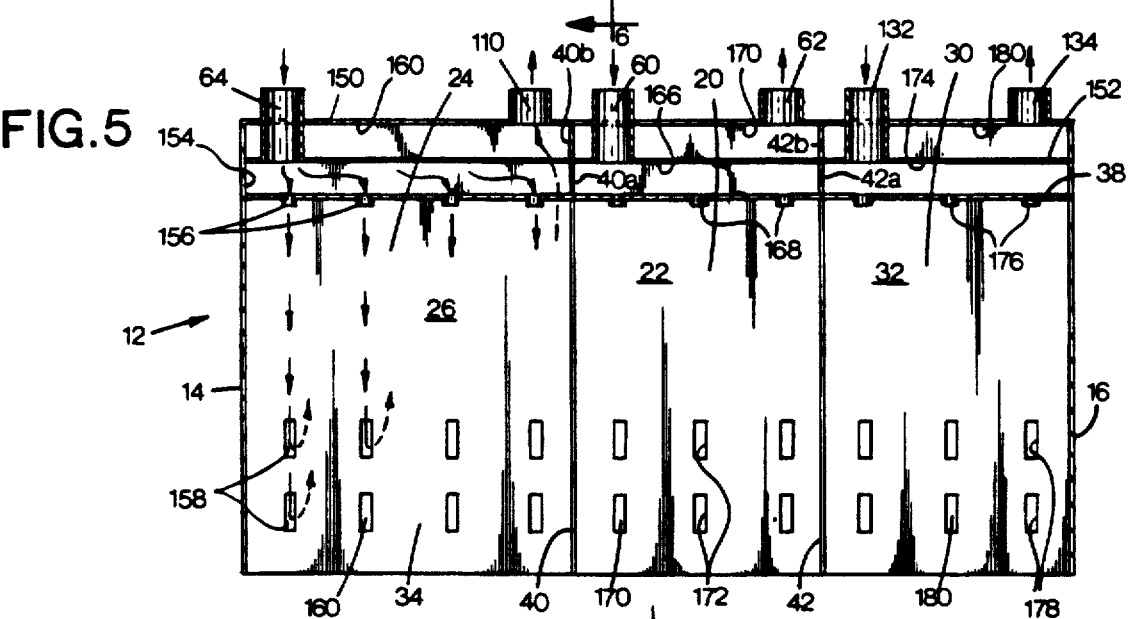
FIG. 5 is a vertical sectional view taken along line 5—5 of FIG. 4.
Figure 6:
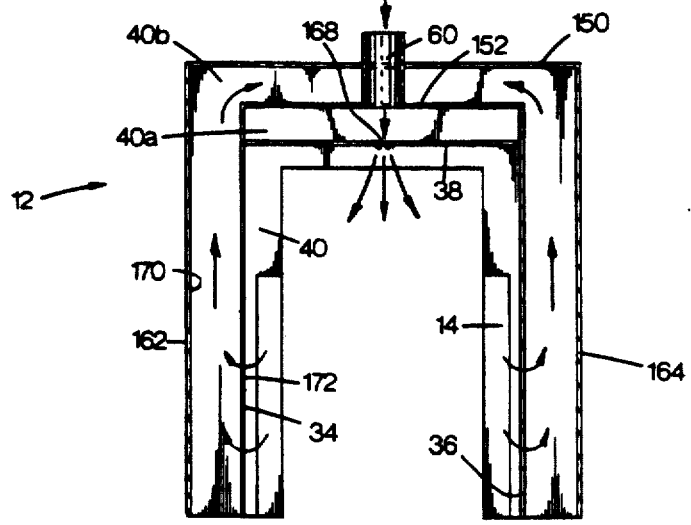
FIG. 6 is a vertical sectional view taken along lines 6—6 of FIG. 4.

Referring also to FIGS. 4–6, the main heating chamber 20, the preheat chamber 24 and the cooling chamber 30 are defined by two interior upright sidewalls 34 and 36 and an interior upper wall 38. The main heating and preheat chambers 20 and 24 may be partially separated by an upright wall 40. Similarly, the heating and cooling chambers 20 and 30 may be partially separated by upright wall 42. Thus, the illustrated shroud 12 serves as a common housing for at least partially enclosing the preheat, main heating and cooling zones.

Before describing in detail the construction of the shroud 12, the gas handling system 48 of the activation apparatus 10 will be described with reference to FIG. 7. The activation apparatus 10 has a main heating chamber hot gas source 50 including a main heating supply blower 52 which blows a hot gas, such as air, across the heating coils of a main heater 54. The heated gas moves through a duct 58 from the main heater 54 through a volume damper 56 in duct 58. The duct 58 is coupled to an inlet 60 of the main heating chamber 20. The moving hot gas is circulated through the main heating zone 22 in a manner described further below, to produce an exhaust gas which exits the shroud 12 through a main heating chamber outlet 62.

The preheating stage 26 has a preheat chamber inlet 64. In an alternative embodiment, the heated exhaust gas may be delivered directly from the main heating chamber outlet 62 to the preheat chamber inlet 64 via ductwork (not shown). In this case, the hot gas source blower 52 receives makeup inlet air directly from the atmosphere.

A heat recycling system is illustrated including recycling means 70 coupled to the main heating chamber outlet 62 via a duct 72. The recycling means has a hot exhaust gas blower 74 that draws the exhausted hot gas from chamber 20. To control the volume of gas removed from the main heating chamber 20, the recycling means 70 has a volume damper 76 in duct 78 exiting the exhaust blower 74. The activation apparatus 10 may also include a heat recovery system 80 including an air-to-air rotary heat exchanger 82. The heat exchanger 82 receives the exhausted hot gas from duct 78 and vents this gas to atmosphere through duct 84. The rotary heat exchanger 82 receives makeup inlet air through duct 86 and heats the makeup air using heat from the exhausted hot gas. The heated makeup inlet air then exits the heat recovery system 80 via duct 88.

Alternatively, at least a portion of the exhausted hot gas may be bypassed around the heat recovery system 80 via bypass duct 90 which interconnects ducts 78 and 88. The bypass duct 90 has a volume damper 92 to control the amount of exhausted hot gas bypassed around the heat recovery system 80.

The illustrated activation apparatus 10 has a preheat gas source 100. The preheat gas source 100 includes a preheat blower 102 which receives the heated inlet makeup gas or the bypassed hot exhaust gas from duct 88. A volume damper 104 regulates the gas flow from the preheat blower 102 to the coils of a preheat heater 106, thereby producing a preheated moving gas. The preheated moving gas is delivered from the preheat gas source 100 to the preheat chamber inlet 64 via duct 108. After the preheat gas is circulated through the preheating zone 106, as described further below, it is exhausted through a preheat outlet 110. The exhausted preheat gas is drawn by the main blower 52 from the preheat outlet 110 to the main heating chamber hot gas source 50 via duct 112.

One form of overall recycling system of the illustrated activation apparatus 10 includes heater means comprising heaters 106 and 54 for reheating the recycled exhaust gas. The recycling system has means, including bypass duct 90 and volume damper 92, for returning at least a portion of the reheated exhaust gas to the heating zone. In the alternative embodiment of FIG. 1 which lacks a preheating stage, ductwork (not shown) couples duct 78 from the recycling means 70 to a main heating chamber hot gas source inlet duct.

In the the alternative embodiment mentioned above, wherein the main heating chamber exhaust gas is delivered to the preheat chamber inlet 64, the apparatus 10 may include a heat recovery system, such as system 80. This heat recovery system would receive the preheat chamber exhaust gas from outlet 110 before venting to atmosphere. An air-to-air rotary heat exchanger, such as exchanger 82, would then heat makeup air received from the atmosphere using heat from the preheat chamber exhaust gas. The hot gas source 50 would then receive the heated makeup air from the rotary heat exchanger.

The activation apparatus 10 also has a cool gas source 120 of moving quench or cooling gas, such as air. A cooling gas supply blower 122 receives makeup or supply air from the atmosphere via duct 124. The makeup air from the cooling supply blower 122 is then cooled, such as by forcing the makeup air across cooling coils of a cooling or refrigeration unit 126. The volume flow of the gas through the refrigeration unit 126 is regulated by volume damper 128 as it exits the refrigeration unit via duct 130. Duct 130 couples the cool gas source 120 a cooling chamber inlet 132 to deliver the moving cooling gas to the cooling zone 32.

After the cooling gas has circulated through the cooling zone 132 as described further below, it is exhausted through a cooling chamber outlet 134. The exhausted cooling gas is delivered from outlet 134 back to the cool gas source 120 via duct 136. A volume damper 138 regulates the volume of cooling gas drawn from the cooling zone 32 by a cooling exhaust blower 140. The exhausted cooling gas is then vented to atmosphere from cooling blower 140 via duct 142.

To prevent overheating within the main heating chamber 20, a bypass duct 144 may be included between the cool gas inlet duct 130 and the hot gas source outlet duct 58. The duct 144 has a volume damper 146 to control flow through the duct.

Now that a suitable overall gas handling system 48 is understood, the construction and operation of the illustrated shroud 12 will be described with reference to FIGS. 4-6. In the illustrated embodiment including the preheating stage 26, the preheated gas is delivered to the preheat chamber inlet 64. The preheat inlet 64 penetrates through an outer upper wall 150 and an intermediate upper wall 152 of the shroud 12 to deliver the preheated gas into a preheat inlet plenum 154. The preheat inlet plenum 154 is bounded at its top and bottom by the respective walls 152, 38, at one end by a section of the wall at entrance end 14, at its other end by an upright wall 40a and at its sides by upper sections of the interior shroud walls 34, 36.

Gas from the preheat inlet plenum 154 is typically directed to the preheat chamber 26 by a gas directing surface having a plurality of nozzles, such as nozzles 156 extending through the inner upper wall 38. The nozzles 156 direct jets of preheat gas at the upper edges $E_1$ and $E_2$ (FIG. 3) of each diaper D being moved through the preheating zone 26 by the transport means 18.

While the nozzles 156 in FIGS. 4-6 are schematically illustrated as circular in nature, slot nozzles may also be used. For example, the slot nozzles may each be three inches long, with a 0.0625 inch nozzle gap. For an eighteen inch long heating chamber 20, such as for the shroud embodiment shown in FIG. 1 without a preheat chamber, the nozzles may be spaced one inch apart along the length of the heating chamber 20. Baffles and other air direction devices may be used in addition to or in lieu of nozzles.

The preheat gas is exhausted from the preheating zone 26 through a plurality of outlet apertures 158 (FIG. 5) through the interior upright sidewalls 34 and 36 and to a preheat outlet plenum 160. The preheat outlet plenum 160 is defined by the interior upright sidewalls 34 and 36, outer sidewalls 162 and 164 of shroud 12, a contact surface 165 (FIG. 7) of stacker S, the shroud upright wall at entrance end 14, an upright wall 40b (FIG. 5) which may be coplanar with wall 40, and the respective outer and intermediate upper walls 150 and 152. Thus, the preheat inlet and outlet plenums are configured in a compact, stacked relationship, one above the other. The exhausted preheat gas is exhausted from the preheat outlet plenum 160 via the preheating chamber outlet 110.

The main heating stage inlet 60 extends through the outer and intermediate upper walls 150 and 152 to deliver the moving heated gas to a main heat inlet plenum 166. The main heat inlet plenum 166 is defined by the inner and intermediate upper walls 38 and 152, sections of walls 34, 36, wall 40a, and an upright wall 42a which may be coplanar with wall 42. An outlet of the main heat inlet plenum serves as inlet means for the main heating zone 22 and may comprise a gas directing surface, such as a surface with a plurality of nozzles 168 extending through the inner upper wall 38. The nozzles 168 direct jets of hot gas toward the edges $E_1$ and $E_2$ of each diaper D (FIG. 3) being moved through the heating zone 22 by the transport means 18.

The main heating chamber has hot gas exhaust means including a main heating zone outlet plenum 170. The outlet plenum receives the hot exhaust gas from the main heating zone 22 through a plurality of apertures 172 extending through the inner upright sidewalls 34 and 36. The hot gas outlet plenum 170 is defined by the sidewalls 34 and 36, the extended upright shroud sidewalls 162 and 164, the stacker contact surface 165 (FIG. 7), the upright walls 40b and 42b, and the outer and intermediate upper walls 150 and 152. The hot exhaust gas is drawn by the exhaust blower 74 from the hot gas outlet plenum 170 through the main heating outlet 62. The illustrated shroud thus also has stacked upper and lower heat plenums 166, 170.

The cooling chamber inlet 132 extends through the outer and intermediate upper walls 150 and 152 to deliver the moving cooling gas to a cooling inlet plenum 174. The cooling inlet plenum 174 is defined by the intermediate upper wall 152, the inner upper wall 38, portions of walls 34, 36, the upright wall 42a, and an upright wall defining the exit end 16 of shroud 12. A gas directing surface such as wall 38 with a plurality of nozzles directs the cool gas flow to the upper edges $E_1$ and $E_2$ of each diaper D being moved through the cooling zone 32 by the transport means 18.

After circulating through cooling zone 32, the cooling gas is exhausted through a plurality of apertures, such as 178, extending through the upright inner sidewalls 34 and 36. The cooling zone includes cooling zone exhaust means comprising a cooling outlet plenum 180 receiving the exhausted cooling gas through apertures 178. The cooling outlet plenum 180 is defined by the inner upright sidewalls 34 and 36, the outer sidewalls 162 and 164, the stacker contact surface 165 (FIG. 7), the upright wall 42b, the upright wall defining the shroud exit end 16, and the outer and intermediate upper walls 150 and 152. The exhausted cooling gas is drawn from the cooling outlet plenum 180 by the cooling exhaust blower 140 through the cooling chamber outlet 134. The plenums 174, 180 are also thus stacked to provide a compact design.

The main heating zone and cooling zone inlet nozzles 168 and 176, illustrated as circular in nature, may also be slot nozzles, as described above for the preheat zone inlet nozzles 156 or other air directing devices. The slot nozzles 168 and 176 may, for example, be spaced one inch apart along the path of travel of the diapers D through the shroud 12.

Figure 7:
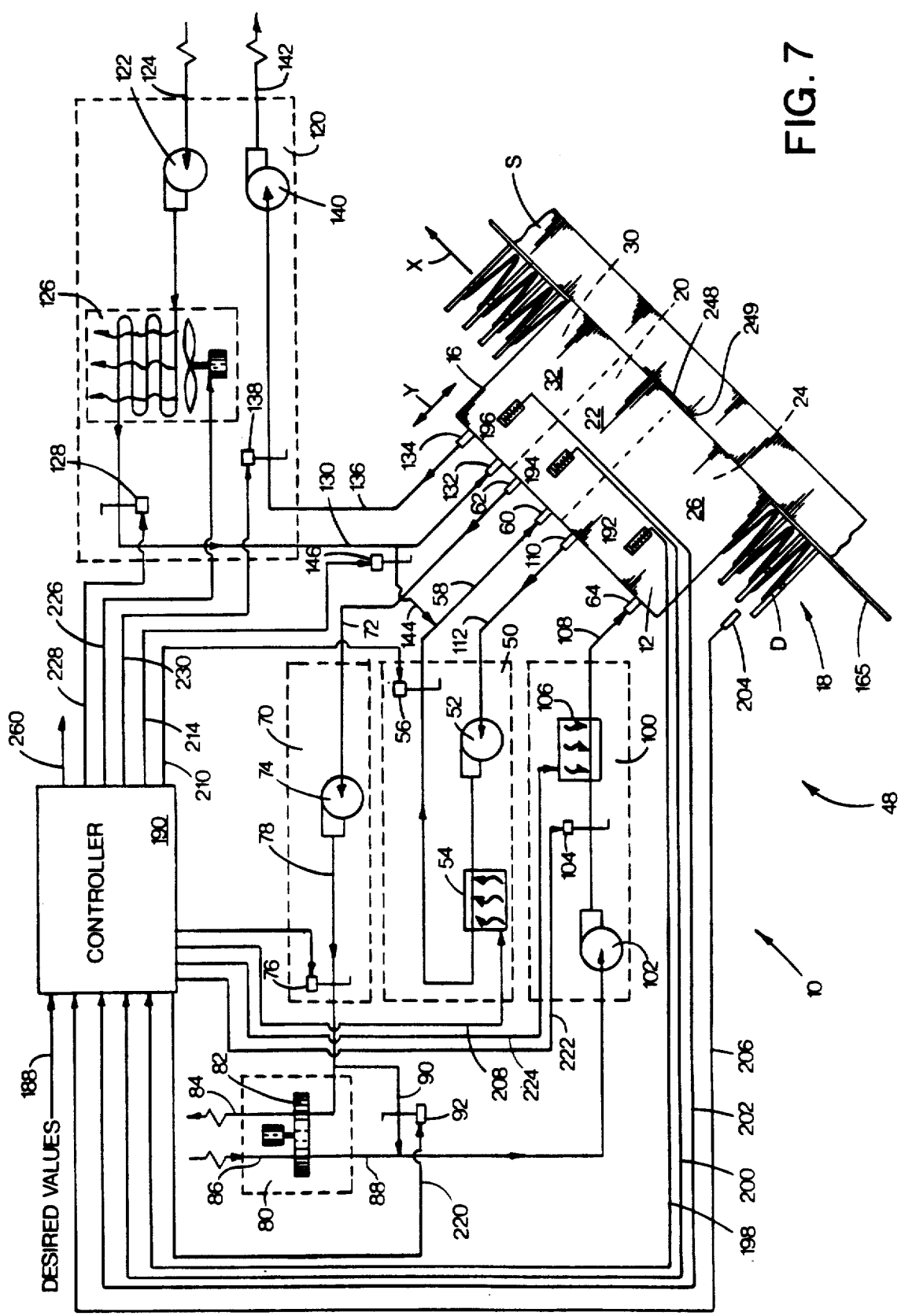
FIG. 7 is a partially schematic diagram of one form of a gas handling system and a control system of the present invention.

The desired operating values within shroud 12 of temperature, gas flow velocity and gas flow volume are furnished as a desired value input signal 188 to a controller 190, shown in FIG. 7. The temperature, gas flow velocity and volume requirements within shroud 12 depend upon the type of thermal film F used and the type of article upon which the elastic band is formed. Thus, the main heating zone 22 has a shrinkage atmosphere with a shrinkage temperature which is sufficiently elevated to activate the heat-sensitive thermal film F to shrink the film to form an elastic band on a given article.

In the disposable diaper example, using Fulflex Blend III as the film F, an acceptable elastic waistband W is formed with a desired shrinkage (or percent elasticity) in excess of twenty-five percent, and with an elastic tension of approximately 280 grams. This acceptable waistband W may be formed by applying hot air at 230° F. for four seconds at a velocity of 1,200 feet per minute (fpm). The time duration during which the heated gas is applied to the waistband portions depends upon the speed with which the transport means 18 moves the diapers D through shroud 12 and the physical length of the heating chamber. For example, the two stage shroud 12 shown in FIG. 1 (having no preheating stage) may be approximately twenty-four inches long, with an eighteen inch long main heating chamber 20 and a six inch long cooling chamber 30. This embodiment requires an air flow of approximately 70 cubic feet per minute (cfm). However, it is believed that suitable elastic film activation may be obtained at temperatures between about 160° F. and about 250° F. Furthermore, suitable results may be obtained at temperatures between 160° F. and 230° F. with increased air velocity, such as on the order of 1,650 fpm.

To control the shrinkage of the elastic film, and arrest or stop the activation process, the diapers D are quenched by transporting them from the heating zone 22 through the cooling zone 32. The cooling zone also advantageously cools the entire diaper, in addition to the waistband area, to minimize and prevent any damage to the balance of the diaper from the elevated temperatures encountered in the heating zone 22.

The quench atmosphere within the cooling zone is at a quench temperature less than that within the heating zone 22. For example, the temperature within the cooling zone 32 may range between about 35° F. and about 100° F. The preheat atmosphere within the preheating stage 26 may be at an intermediate preheat temperature between the shrinkage temperature in the heating zone 22 and the quench temperature in the cooling zone 32.

The air flow velocities and volumes within the preheat chamber 24 and cooling chamber 30 may be the same as, or different than the values within the heating zone 22. However, in the preferred embodiment, the shroud is neutrally or overpressurized so equal or greater volumes of air are supplied to each chamber 20, 24 and 30 than are removed via the outlets from each respective chamber.

The desired operating conditions, such as those outlined above for forming disposable diaper elasticized waistbands, are set by an operator or by automated means (not shown) to provide the desired value input signal 188 to controller 190. To control and maintain the desired operating conditions, the controller 190 receives a series of input signals from various sensors and monitors. For example, the temperature within each of the preheating, main heating, and cooling zones 26, 22 and 32, are monitored by temperature monitor means, such as internal thermocouples (not shown) within each stage. The thermocouples within the preheating, main heating, and cooling zones 26, 22 and 32, may supply output readings to temperature gauges 192, 194 and 196, respectively. The controller 190 receives preheat, main heating, and cooling temperature signals 198, 200 and 202 from the preheat, main heating and cooling zone thermocouples, respectively.

A speed monitor or sensor 204 is positioned to monitor the speed of the transport means 18 carrying the diapers D through shroud 12. The speed sensor 204 may be an optical or mechanical transducer which provides a speed input signal 206 to controller 190.

To monitor the velocity of the gas flow within the preheat, main heating, and cooling chambers 24, 20 and 30, gas velocity monitoring means, such as vane anemometers (not shown) may be positioned at appropriate locations within shroud 12, or at other locations within the gas handling system 48. The vane anemometers generate flow input signals (not shown) corresponding to the measured gas flows. The flow input signals are received and processed by controller 190, and along with desired values signal 188, the speed sensor signal 206 and the temperature signals 198, 200 and 202 to regulate the activation apparatus 10. The controller 190 may be a computerized analog or digital control system, such as a microprocessor, or a portion of the control system for the overall diaper assembly line.

The temperature and flow of the moving heated gas through the main heating zone 22 are controlled by heating zone temperature and flow control means comprising the controller 190 generating a plurality of shrinkage control signals coordinated to provide the desired shrinkage atmosphere. The controller 190 controls the inputs to the main heating zone 22 by providing a main heater control signal 208 to the main heater 54, and a damper control signal 210 to the volume damper 56. Controller 190 provides a damper control signal 212 to volume damper 76 to control the volume of exhaust gas drawn from the main heating zone 22 by the exhaust blower 74.

During normal operation, volume damper 146 is closed, preventing cooling gas from flowing through bypass duct 144. In an overheat emergency, the thermocouples within the main heating zone 22 detect a dangerously high temperature and provide a corresponding high temperature input signal 200 to controller 190. In response, the controller 190 sends an overheat emergency damper signal 214 to the overheat emergency bypass volume damper 146. The emergency signal 214 fully opens the damper 146 to dump cooling gas to the main heating zone input 60 which cools down the heating zone 22.

The temperature and flow of preheat gas moving through the preheating stage 26 are controlled by preheat zone temperature and flow control means comprising the controller 190 generating a plurality of preheat control signals coordinated to provide a desired preheat atmosphere. The preheat atmosphere is determined by the settings of the preheat heater 106, input volume dampers 92 and 104, and output volume damper 56 which controls the volume of gas drawn from the preheat chamber by blower 52. The controller 190 controls the inputs to the preheat zone 26 by providing damper control signals 220 and 222 to dampers 92 and 104, respectively. The controller 190 controls the preheat heater 106 with a preheat temperature control signal 224.

The temperature and flow of cooling gas through the cooling zone 32 are controlled by cooling zone temperature and flow control means comprising the controller 190 generating a plurality of quench control signals coordinated to provide a desired quench atmosphere. The quench atmosphere is determined by the settings of refrigeration unit 126, volume dampers 128 and 138, and during an overheat emergency, by the overheat emergency bypass volume damper 146. The controller 190 controls the refrigeration unit 126 with a cooling zone temperature control signal 226. The controller provides volume dampers 128 and 138 with damper control signals 228 and 230, respectively.

The activation apparatus 10 may also include variable lateral compactor, such as a side edge compactor 240, for spreading apart the edges $E_1$ and $E_2$ to expose the interior region R of the diaper D being transported by the article transporter 18 through shroud 12. The illustrated compactor 240 has two opposing horizontal compression bars 242 and 244. The compression bars 242 and 244 are each mounted to an L-shaped mounting member. For example, the compression bar 244 is mounted to vertical leg 246 which joins horizontal leg 248 of the L-shaped mounting member. The contact surface 165 of stacker S has a recess 249 to slidably receive horizontal leg 248 for motion in a direction indicated by arrow Z in FIG. 3. The recess 249 is sized so the horizontal mounting portion 248 of the compactor is flush with the stacker surface 165 to provide a seal along a portion of the bottom edge along the shroud 12.

Referring to FIGS. 2 and 3, the transport means 18 includes an endless belt 250 having a plurality of separator plates, such as 252a, 252b, 252c and 252d projecting outwardly therefrom. The diapers D may be received between each of two adjoining plates, such as 252a and 252b, from a diaper assembly line (not shown). Each separator plate 252 includes two opposing, compression bar receiving, recesses or slots 254 and 256. Upon entering the shroud 12, the compression bar 242 is received by slots 254 of each separator plate, and compression bar 244 is received by slots 256.

At the shroud entrance end 14, the compression bars 242 and 244 have a gradual outward curve, such as curve 258 on bar 244. The curve 258 allows the compression bars to gradually engage the sides of diaper D as it enters the shroud, and to gradually compress the diaper D in a lateral direction generally parallel to the waistband edges $E_1$ and $E_2$. This lateral compression forces apart edges $E_1$ and $E_1$ to expose the inner region R and the inner layer $L_1$ of the diaper to the preheat and main heating gases.

It is apparent that other side edge compactors 240 may also be used, such as one having a fixed side (in lieu of compression bar 242) against which the diaper D is compressed by a variable compression member (not shown). Other side edge compactors may be used to gather the diaper body B along the edges $E_1$ and $E_2$, with such compactors positioned to direct a compacting force against the side edges of the diaper. For example, air jets (not shown) may be used to provide the compactor compacting force.

The variable compactor 240 may be controlled by compression control means, such as a hydraulic or pneumatic compression actuator (not shown), for moving the compression bars 242 and 244 as indicated by arrow Z. For example, the controller 190 provides a compression control signal 260 to the drive compactor actuator (not shown). Thus, a desired degree of compression may be imparted to the edges $E_1$ and $E_2$.

In this manner, the separation of the first second edges $E_1$ and $E_2$ allows the moving heated gas to enter the interior region R of the diaper. The moving heated gas activates the first and second heat-sensitive thermal films $F_1$ and $F_2$ to shrink and form the first and second elastic waistbands $W_1$ and $W_2$, respectively. The exposure of the non-woven inner layer $L_i$ to the heated gas is believed to provide for quicker activation of the thermal film F. Furthermore, the compression of the diapers D by the compactor 240 minimizes the tendency of the filler layer $L_f$ to retard contraction of the thermal film F. Thus, the pregathering or bunching of the body of the diaper at the edges $E_1$ and $E_2$ by compactor 240 promotes more rapid activation of film.

In operation, the activation apparatus 10 is mounted to a stacker S which serves as transporter means for transporting the diapers D through shroud 12. The shroud 12 may be either permanently attached to stacker S, or may be raisable therefrom in a direction indicated by arrow Y by raising actuator means (not shown). The raising actuator means may be responsive to a shroud raising and lowering control signal (not shown) from controller 190.

For example, during start-up, it may be advantageous to have the shroud 12 raised above the stacker contact surface 165 while the preheat, main heat and cooling gases are brought to temperature. Once the desired temperature and air flow are reached, the shroud 12 is lowered into position adjacent the stacker contact surface 165. During emergency conditions, such as over-temperature, fire and the like, the shroud 12 may be raised above stacker S to minimize damage to the diapers D moving therethrough.

In discussing the operation of the activation apparatus 10, a first method is also illustrated of activating a heat-sensitive thermal film F attached to a first edge of a body of an article, such as diaper D to form an elastic waistband W. In a two stage shroud, such as illustrated in FIG. 1, in a heating step conducted within the heating chamber 20, the edges $E_1$ and $E_1$ of the article are heated to a first temperature. Thermocouples within the heating zone monitor the temperature therein and provide a temperature signal to temperature gauge 194 and the signal 200 to controller 190. In response to the temperature input signal 200 and the desired value signal 188, the controller generates the main heater signal 208 to drive the main heater 54. The desired first temperature is chosen to be sufficiently elevated to activate the particular type of heat-sensitive thermal film F in a given article to form the elastic band, such as waistband $W_1$ and $W_2$.

In a cooling step, edges $E_1$ and $E_2$ are actively or force cooled after the heating step to a second temperature which is less than the first temperature to arrest the shrinkage of the heat-sensitive film F. The cooling step may include the step of directing the cooling gas at the second temperature toward edges $E_1$ and $E_2$ of the diaper. Thermocouples within the cooling zone 32 monitor the temperature therein which may be read on temperature gauge 196. The cooling zone thermocouples provide a cooling zone temperature signal 202 to controller 190. Controller 190 controls the temperature within the cooling zone by providing cooling damper control signals 228 and 230 to control volume dampers 128 and 138, respectively. The controller 190 also controls the temperature within the cooling zone by driving the refrigeration unit 126 with the refrigeration control signal 226.

To activate many suitable thermal films F, it is believed that the heating step comprises the step of supplying a heated gas at a first temperature between about 160° F. and about 250° F. to the heating zone 22. Heated gas jets are directed toward edges $E_1$ and $E_2$ by nozzles 168. The cooling step further includes the step of supplying a cooling gas at a second temperature to the cooling zone 32. For many suitable films F, the second temperature is between about 35° F. and about 100° F.

For a three stage shroud, such as shown in FIGS. 3–7, the method also includes the steps of preheating edges $E_1$ and $E_2$ to a third intermediate temperature which is between the first and second temperatures. Thermocouples monitor the temperature within the preheating stage 26 which may be read at temperature gauge 192. The thermocouples provide a preheat stage temperature signal 198 to controller 190. To maintain the preheating zone temperature at a desired value, controller 190 provides a preheating heater control signal 224 to the preheat heater 106. The controller 190 also provides volume damper control signals 220, 222, and 210 to volume dampers 92, 104 and 56, respectively.

In a recycling step, the exhaust gas from the main heating zone 22 is received by recycling means 70 to provide a preheating heat source, such as by exiting through the rotary heat exchanger 82 to atmosphere, or by being an input to the preheat gas source 100, via bypass duct 90.

The method also includes the steps of conducting the heating and cooling steps within at least one chamber, such as shroud 12, having a heating zone 22 and a cooling zone 32 therein. The method also includes the step of transporting the diaper D from the heating zone 22 through the cooling zone 32 using transporter 18.

The method may also include a step of laterally compressing the body B of the diaper in a direction generally parallel to edges $E_1$ and $E_2$ during the heating step to aid in formation of the elastic band. The step of compressing is accomplished by the horizontal compression bars 242 and 244 laterally compressing the diapers after entering the shroud entrance end 14 or by any other suitable mechanism for applying a force to the sides of a folded diaper. The degree of compression may be adjusted by the compactor controller signal 260. The control signal 260 positions the compactor 240 at desired locations by moving the compactor in the direction indicated by arrow Z.

A second method of activating a heat-sensitive thermal film F attached to edges, such as diaper edges $E_1$ and $E_2$, includes the steps of heating the edges $E_1$ and $E_2$ as described above. During the heating step, a compressing step of laterally compressing edges $E_1$ and $E_2$ of the article is performed to aid in formation of the elastic waistbands $W_1$ and $W_2$.

The second method may also include the steps of laterally compressing the diapers D to separate the first and second edges $E_1$ and $E_1$ to expose the interior region R of diaper D. The heating step further includes the steps of directing a moving heated gas at a temperature of at least the first temperature toward the first and second edges $E_1$ and $E_2$ of diaper D. In this manner, the moving heated gas is allowed to enter the interior region R of the article to activate the first and second heat-sensitive thermal films F. This method substantially simultaneously forms the first and second elastic waistbands $W_1$ and $W_2$.

Having illustrated and described the principles of my invention with respect to a preferred embodiment, it should be apparent to those skilled in the art that my invention may be modified in arrangement and detail without departing from such principles. For example, a variety of other articles may be manufactured using these principles, which may require modifications of the heating shroud, article transporter, separator plates 252, the compression bars 242 and 244, etc. Furthermore, suitable material substitutions and dimensional variations for the components of the activation apparatus may be made. I claim all such modifications falling within the scope and spirit of the following claims.

I claim:

1. An elastic band heat activation apparatus for activating a heat-sensitive thermal film attached to a first edge of a body of an article to form an elastic band along the first edge of the article, the apparatus comprising:

at least one chamber;

the chamber having a heating zone with an atmosphere at a first temperature sufficiently elevated to activate the heat-sensitive thermal film to shrink the film to form an elastic band;

a cool gas source of cooling gas at a temperature which is less than ambient temperature;

the chamber having a cooling zone coupled to the cool gas source for receiving cooling gas to provide a cooling zone with an atmosphere at a second temperature which is less than the first temperature; and an article transporter for transporting the article first through the heating zone to activate the heat-sensitive thermal film and then through the cooing zone to arrest the shrinkage of the heat-resistance thermal film, thereby forming the elastic band.

2. An apparatus according to claim 1 further including:

a hot gas source of moving heated gas at a temperature of at least the first temperature coupled to the heating zone; and the cool gas source comprising a source of moving cooling gas coupled to the cooling zone.

3. An apparatus according to claim 2 wherein: the first temperature is between about 160° F. and about 250° F.; and the second temperature is between about 35° F. and about 100° F.

4. An apparatus according to claim 1 wherein the chamber comprises a common housing for at least partially enclosing the heating and cooling zones.

5. An apparatus according to claim 1 wherein:

the chamber comprises a common housing for at least partially enclosing the heating zone and the cooling zone;

the apparatus further includes a hot gas source of heated gas;

the heating zone includes hot gas inlet means coupled to the hot gas source for receiving and directing the heated gas toward the first edge of the article; and the cooling zone includes cool gas inlet means coupled to the cool gas source for receiving and directing the cooling gas toward the first edge of the article so as to actively cool the film.

6. An apparatus according to claim 5 wherein:

the chamber includes hot gas exhaust means for exhausting the heated gas as an exhaust gas after the heated gas has activated the heatsensitive thermal film; and the apparatus further includes a hot gas recycling system coupled to the hot gas exhaust means for receiving the exhaust gas, the recycling system including heater means for reheating the exhaust gas and means for returning at least a portion of the reheated exhaust gas to the heating zone.

7. An apparatus according to claim 5 wherein:

the first temperature is between about 160° F. and about 250° F.; and the second temperature is between about 35° F. and about 100° F.

8. An apparatus according to claim 5 wherein:

the hot gas inlet means comprises a first plenum having a first plenum outlet, with the first plenum receiving heated gas from the hot gas source, and the first plenum outlet including a gas directing surface having a plurality of first apertures therethrough interconnecting the first plenum with the heating zone;

the cool gas inlet means comprises a second plenum having a second plenum outlet, the second plenum receiving cooling gas from the cool gas source, and the second plenum outlet including a gas directing surface having a plurality of second apertures therethrough interconnecting the second plenum with the cooling zone; and the first and second apertures are positioned to direct the respective heated gas and cooling gas as gas jets only toward the first edge of the article along which the heat-sensitive thermal film is attached while the article is transported by the transport means through the respective heating and cooling zones.

9. An apparatus according to claim 1 wherein the heating zone comprises a preheating stage and a main heating stage, the main heating stage having an atmosphere at the first temperature, and the preheating stage having an atmosphere at a third intermediate temperature being between the first and second temperatures.

10. An apparatus according to claim 2 further including:

heating zone flow control means for controlling a rate of flow of the moving heated gas from the hot gas source through the heating zone;

cooling zone flow control means for controlling a rate of flow of the moving cooling gas from the cool gas source through the cooling zone;

heating zone temperature monitor means for monitoring the first temperature;

heating zone temperature control means for controlling the temperature of the heated gas from the hot gas source in response to the heating zone temperature monitor means;

cooling zone temperature monitor means for monitoring the second temperature; and cooling zone temperature control means for controlling the temperature of the cooling gas from the hot gas source in response to the cooling zone temperature monitor means.

11. An apparatus according to claim 1 wherein:

the article includes a first heat-sensitive thermal film attached to the first edge to form a first elastic band along the first edge, the body of the article having a second edge opposing the first edge, and the article including a second heat-sensitive thermal film attached to the second edge to form a second elastic band along the second edge of the article, the article being transported by the article transporter in a folded condition with the first edge adjacent the second edge and defining therebetween an article interior region; and the apparatus further includes compression means for spreading apart the first and second edges while the article is transported by the article transporter through the heating zone to expose the interior region of the article to activate the first and second heat-sensitive thermal films to form the first and second elastic bands.

* * * * *